United States Patent [19]

Brushwyler et al.

[11] 4,018,661
[45] Apr. 19, 1977

[54] INSTRUMENT SENSOR ASSEMBLY

[75] Inventors: Gordon R. Brushwyler, Anaheim; Timothy F. Scott, Brea, both of Calif.

[73] Assignee: Robertshaw Controls Company, Richmond, Va.

[22] Filed: Sept. 4, 1975

[21] Appl. No.: 610,278

[52] U.S. Cl. .................... 204/195 F; 204/195 G; 204/195 R

[51] Int. Cl.² .................................... G01N 27/46

[58] Field of Search ....... 204/195 R, 195 F, 195 G, 204/195 L, 195 M

[56] References Cited

UNITED STATES PATENTS

| | | | |
|---|---|---|---|
| 3,235,477 | 2/1966 | Keyser et al. | 204/195 P |
| 3,434,953 | 3/1969 | Porter et al. | 204/195 G |
| 3,467,590 | 9/1969 | Gibson et al. | 204/195 L |
| 3,530,056 | 9/1970 | Haddad | 204/195 F |

FOREIGN PATENTS OR APPLICATIONS

| | | | |
|---|---|---|---|
| 1,039,260 | 9/1958 | Germany | 204/195 G |

*Primary Examiner*—T. Tung
*Attorney, Agent, or Firm*—Fulwider, Patton, Rieber, Lee & Utecht

[57] ABSTRACT

There is disclosed an instrument probe assembly that is suited for the measurement of a variable of a flowing liquid stream which contains suspension of debris and foreign matter. The instrument probe assembly includes a housing having a closed end for immersion in the liquid with a concavity in the closed lower end having sidewalls inclined at an acute angle to the longitudinal axis of the housing and at least one through opening in a sidewall of the concavity to receive at least one probe member which is sensitive to a variable of the liquid with its exposed surface generally continuous with the sidewall. The probe member assembly is employed with a pH meter that includes a sensing electrode in the concavity with the reference electrode mounted within an annular chamber of the housing and having the reference electrolyte in contact with the liquid through a porous disk which is mounted in the through opening in the sidewall of the concavity. The resultant assembly is ideally suited for measurements of a flowing liquid stream that contains debris and foreign suspended matter, e.g., process streams of a sewage plant, since the concavity of the probe assembly introduces a circulatory motion to the liquid within the concavity and this motion prevents the accumulation of debris and foreign matter about the surfaces of the sensing electrode and reference junction of the cell.

11 Claims, 5 Drawing Figures

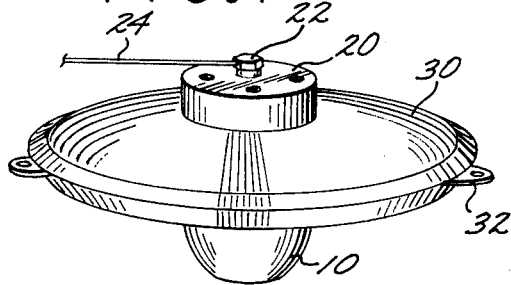
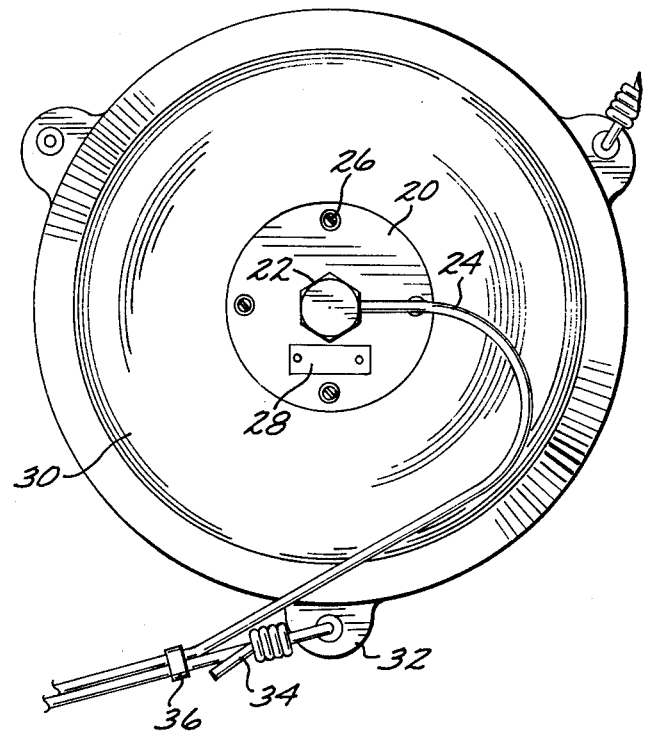
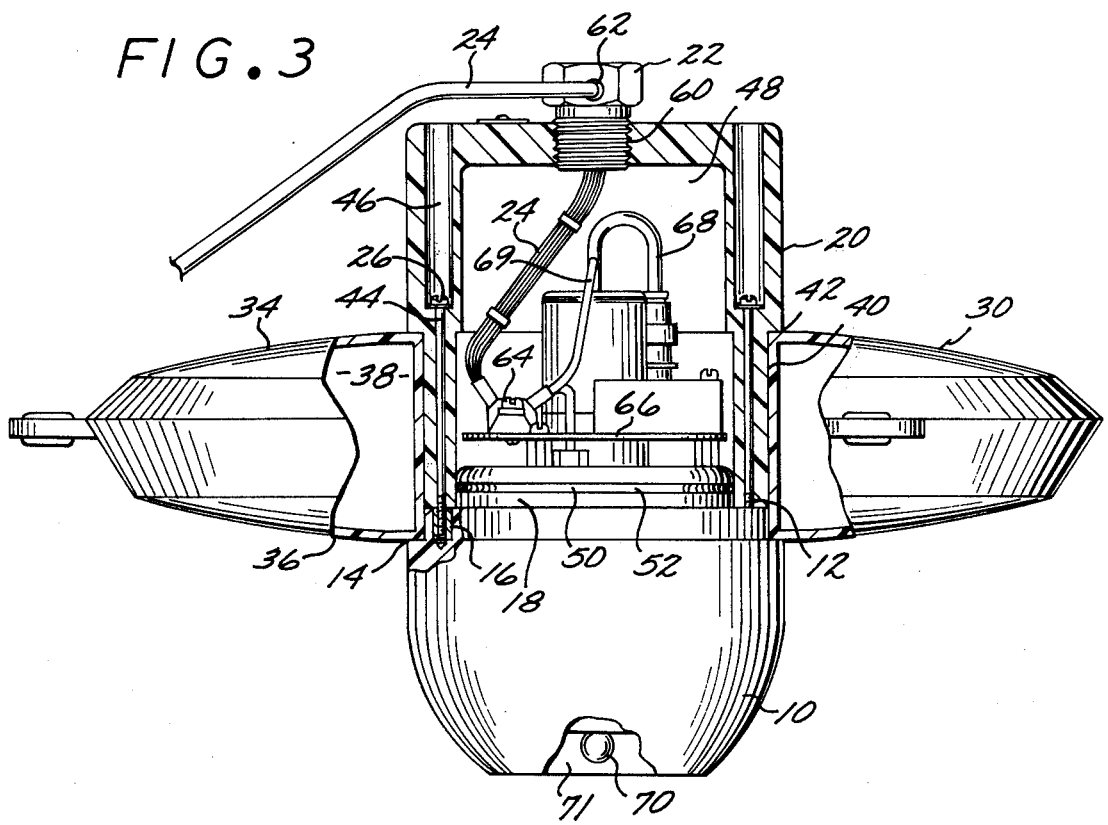

INSTRUMENT SENSOR ASSEMBLY

BACKGROUND OF THE INVENTION

1. Field of the Invention

This invention relates to an instrument probe assembly and, in particular, to an instrument probe assembly ideally suited for a pH cell used in liquids containing debris and suspended foreign matter.

2. Description of the Prior Art

Considerable difficulty is experienced in the measurement of variables of a liquid stream which contains suspended solids and debris. This problem is particularly acute with instruments having sensing elements such as electrodes which generate a signal proportional to the exposed surface of the element, as typical of electrodes of a pH meter having a reference electrode with a porous junction and a sensing electrode that are in contact with the process liquid. Fouling of the electrode or junction surfaces with debris and foreign matter from the liquid interferes with the response of the electrodes and causes erroneous determinations.

Some attempts have been made to obviate the difficulties by providing a perforated circular shield around the sensing electrode and reference junction of a probe assembly for a pH meter. When this device is employed with a liquid stream having a substantial quantity of suspended debris such as a raw sewage stream, the cylindrical shield rapidly fills with solids, clogging the electrode surfaces and requiring frequent maintenance and cleaning.

BRIEF STATEMENT OF THE INVENTION

This invention comprises an instrument probe assembly having a housing with a closed end for immersion in a liquid and bearing a concavity therein with sidewalls inclined at an acute angle to the longitudinal axis of the housing. At least one through opening is provided in a sidewall of the concavity to communicate with an annular chamber within the housing. The annular chamber receives an electrolyte and the reference electrode of a pH cell. The sensing electrode of the cell is mounted in a central, through opening of the housing and projects into the concavity. The concavity induces a circular motion of the liquid flowing past the assembly so that the liquid washes the sensing surfaces of the sensing electrode and the reference junction and keeps these elements clean of solids and debris.

In its preferred embodiment, the housing is secured to a cylindrical cap to form a chamber therein for receiving the electrical circuit elements of the cell. The assembly of cap and housing are preferably secured in the central opening of an annular flotation collar which supports the probe assembly in a liquid body and protects the probe member from blows and collisions with floating debris or walls of the process equipment.

BRIEF DESCRIPTION OF THE DRAWINGS

The invention will be described with reference to the figures of which:

FIG. 1 is a perspective view of the probe member and flotation collar assembly;

FIG. 2 is a plan view of the assembly of FIG. 1;

FIG. 3 is a partial sectional elevation view of the assembly of FIG. 1;

DESCRIPTION OF PREFERRED EMBODIMENTS

Figure 4:
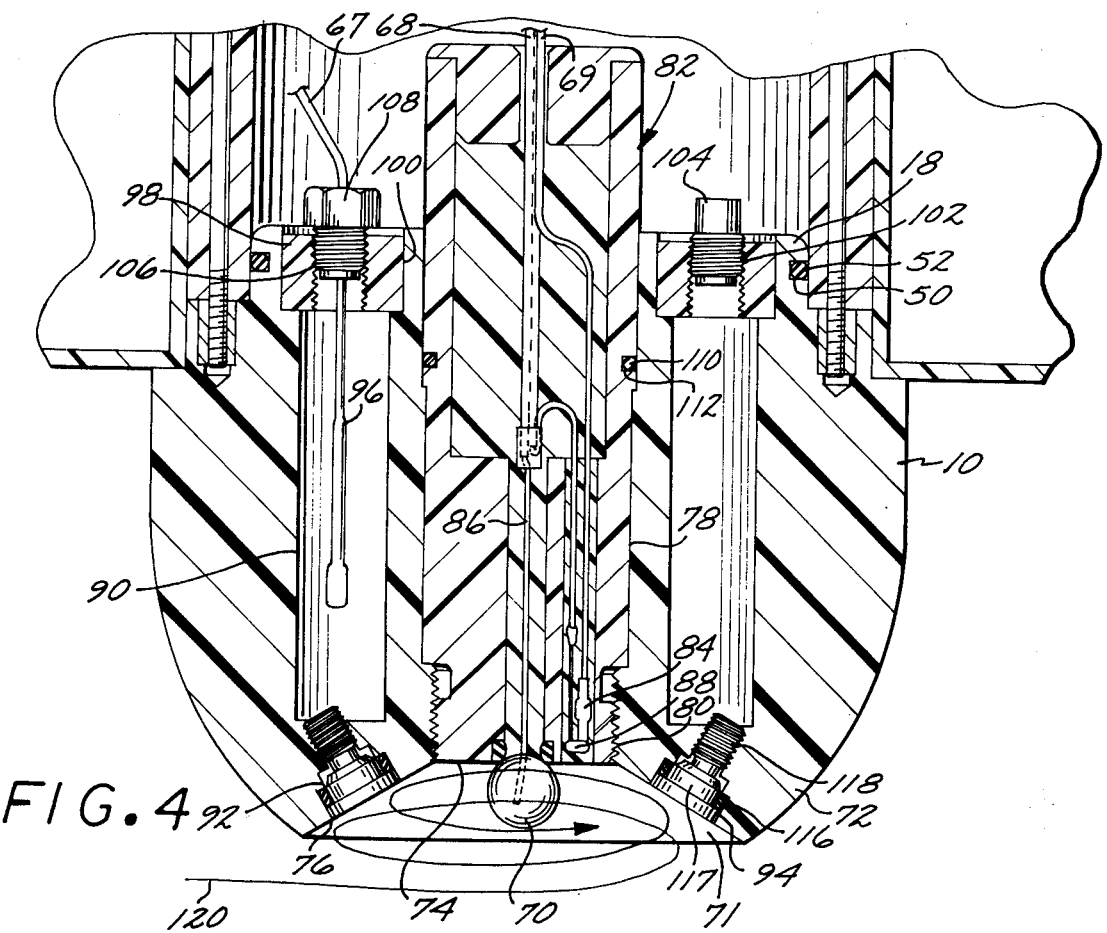
FIG. 4 is a sectional elevation view of the probe member housing in the assembly.

Referring now to FIG. 1, the invention is illustrated as comprising a probe housing 10 having a generally bulbous undersurface with a cylindrical cap 20 and surrounded by an annular flotation collar 30. The flotation collar bears a plurality of tabs 32 which serve as eyelets or securing cables, wires and the like. The cylindrical cap 20 bears a central plug 22 which receives the instrument lead wires 24 that extend to the instrument probe electrodes of the unit.

Referring now to FIG. 2, the unit embodying the invention includes an annular flotation collar 30 that is secured in the assembly about the cap member 20. The cap member 20 is secured to the probe housing 10 by a plurality of tie bolts 26 that extend longitudinally into threaded bores carried in the housing 10. The eyelets in tabs 32 of the flotation collar 30 are secured by one or more cables 34 and the instrument lead wires 24 can be conveniently secured by a snap ring 36 and the like to the cables 34.

Referring now to FIG. 3, the cap 20 can be seen to be generally cylindrical with its lower portion 40 of slightly lesser outside diameter to provide a shoulder 42. The housing 10 also bears a boss 12 of lesser outside diameter to provide a generally continuous cylindrical surface when mated with the sidewall portion 40 of cap 20. Flotation collar 30 surrounds the boss 12 and portion 40 of the cap and is retained by the shoulders 42 and 14 of these members.

The housing 10 bears a plurality of peripherally disposed bores in which are seated the internally threaded nut members 16 to removably secure tie bolts 26 which extend through bores 44 coextensively with the portion 40 of cap 20. The bolts 26 are seated in counterbores 46 disposed about the periphery of cap 20. This secures the cap 20 to housing 10 and secures collar 30 in the assembly.

Collar 30 can comprise any flotation member such as a solid form member of a closed cell plastic foam and the like or, as illustrated, can be of hollow form with top wall 34 and bottom wall 36 secured together, enclosing sealed chamber 38 for flotation of the assembly.

Housing 10 bears an upper boss 18 which has an annular groove 50 in which is seated an O-ring 52 that resiliently seals against the inner wall of cap 20 to provide a sealed chamber 48 within this cap. As previously mentioned, plug 22 is carried by the top surface of cap 20. The top wall of cap 20 is bored at 60 and internally threaded to receive the threaded shank of plug 22. Plug 22 has a through passageway 62 for receiving lead wires 24 which extend into chamber 48 and into contact with a connector panel 64 on platform 66. Lead 67 extends from terminal connector strip 64 to the reference electrode of the cell and lead 68 extends to the sensing electrode 70 located in the concavity 72 on the lower surface of housing 10.

Referring now to FIG. 4, the construction of housing 10 will be described in greater detail. As there illustrated, housing 10 has a generally bulbous lower portion 72 and bears a concavity 71 on its undersurface. The concavity has a centrally recessed portion 74 with sidewalls 76 which are at an acute angle of inclination to the major axis of housing 10. The concavity 71 can also be curvilinear in cross section, e.g., arcuate, ellipsoidal, etc., and should have the sidewalls 76 of its lower portion formed with a tangent thereto at an acute angle of inclination to the major axis of the housing. Housing 10 has a central through opening 78 which is counterbored at 80 and threaded with internal threads for removably securing the sensing electrode subassembly 82.

The electrode subassembly 82 is generally tubular in construction and has a threaded neck 84 for engaging the internal threads of counterbore 80. The sensing electrode 70 is a conventional electrode used for a pH meters having a glass membrane enclosing an electrolyte. Electrode lead 68 extends from the electrode through a central bore in tubular member 82. Preferably, the subassembly also contains a temperature compensating element, e.g., thermistor 88 which is connected in circuit to the shield wire of lead 68 of the electrode 70 and by lead 69 extending to the terminal connector strip 64, previously described.

Housing 10 has an annular chamber 90 which coaxially surrounds the through passageway 78. The annular passageway 90 is coextensive with the length of housing 10 and terminates within housing 10 in proximity to the inclined sidewalls 76 of the concavity 71. At least one through opening 92 is provided in a sidewall, communicating into the annular chamber 90 and, preferably, one or more additional through openings 94 are similarly provided. The annular chamber 90 contains the reference electrolyte for the pH cell.

A reference electrode 96 is positioned within the electrolyte in the chamber and the annular chamber is sealed by ring 98 which is placed within annular groove 100 about the upper edge of the annular chamber. The annular ring bears a through opening 102 with internal threads for receiving plug 104 which is threaded to engage the internal threads of the through opening and provide a sealing closure member for access to the chamber. The ring is also bored at 106 and internally threaded to receive plug 108 that has a central bore to receive lead 67 that extends from the terminal connector strip 64.

The entire assembly is sealed by members such as O-ring 110 that is seated in an annular groove 112 about the tubular member 82 and the aforementioned O-ring 52 which is seated in the annular groove 50 about the upper boss 18 of housing 10.

The through openings such as 94 and 92 are closed with porous disk members 114 that are seated in the through openings and sealed by O-ring 116. The porous disks 114 are carried in plugs 117 having a threaded shank 118 which is turned into engagement with internal threads on the through openings 92 and 94. The porous disks 114 of plugs 117 provide the reference junction for the cell of the pH meter.

Figure 5:
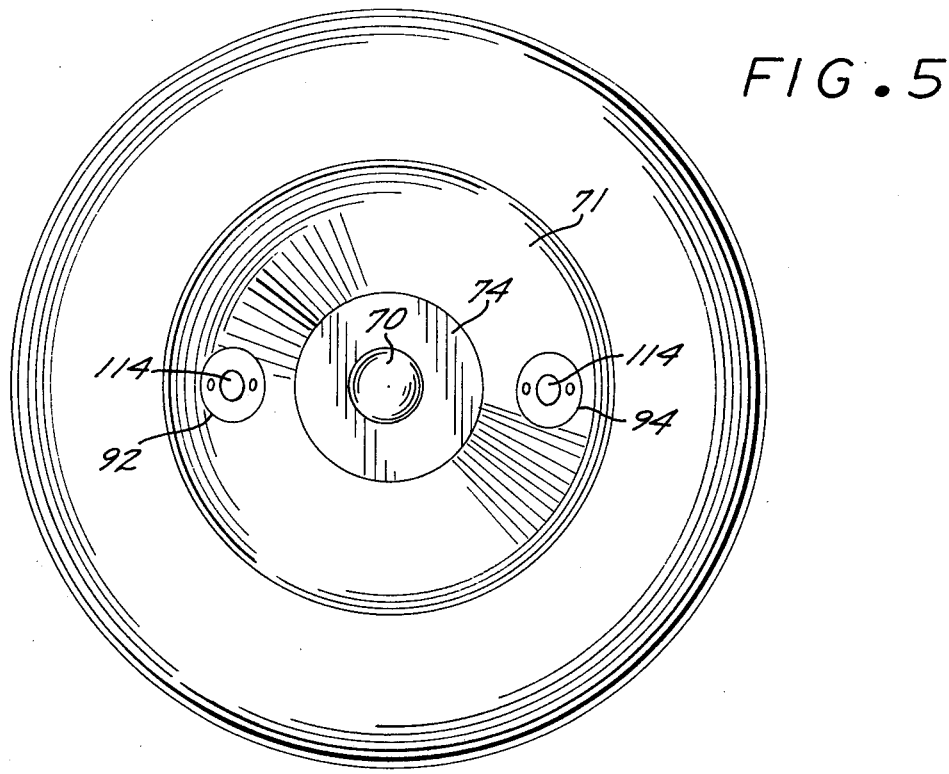
FIG. 5 is a view of the undersurface of the probe member housing of FIG. 4.

The undersurface of the housing 10 is also illustrated in FIG. 5 where the concavity 71 can be seen to have a generally flat central surface 74 and through openings 92 and 94 bearing plugs 117.

The concavity 71 induces eddy currents in fluid flowing past the immersed housing 10. The general configuration of these eddy currents is shown by the arrowhead line 120 as a generally helical flow that passes about the inclined surfaces of the concavity 71 and about the sensing electrode 70 that protrudes from the central portion 74 of the concavity. The effect of the swirling motion of the fluid is to increase the velocity of the fluid past the sensing electrode 70 and the reference junctions defined by porous disks 114. The currents induced into the flowing liquid are effective to remove debris and foreign matter from the sensitive surface areas of the cell.

The invention has been described with reference to the presently preferred and illustrated embodiments. It is not intended that the invention be unduly limited by this description of the preferred embodiments. Instead, it is intended that the invention be defined by the means, and their obvious equivalents, set forth in the following claims.

What is claimed is:

1. An instrument probe assembly comprising:
   a. a probe member housing having a closed end for immersion in a liquid;
   b. an open-ended concave recession in the closed lower end of said housing having a centrally recessed portion with an annular sidewall thereabout, inclined to the longitudinal axis of said housing;
   c. at least one through opening in the sidewall of said concave recession; and
   d. a probe member mounted for exposure to said liquid seated in said through opening and having an exposed surface generally continuous with said sidewall.

2. The instrument probe assembly of claim 1 including a second probe member carried in a through opening located in said centrally recessed portion of said concave recession and protruding into said recession.

3. The instrument probe assembly of claim 2 wherein said second probe member is the sensing electrode of a pH cell and said first probe member comprises a reference junction communicating with the reference electrode of said cell.

4. The instrument probe assembly of claim 3 including a second through opening in the sidewall of said concave recession and an additional reference junction seated therein.

5. The instrument probe assembly of claim 3 wherein said housing has a central through passageway for receiving said sensing electrode and a coaxial annular chamber and said through opening in the sidewall of said concave recession communicates with said coaxial annular chamber.

6. The instrument probe assembly of claim 5 wherein said sensing electrode is mounted in a tubular member having a threaded neck and said central through passageway is internally threaded to removably secure said tubular member.

7. The instrument probe assembly of claim 5 wherein said annular chamber bears a cover ring fixedly secured thereto and having at least one through opening for receiving the reference electrode of said pH cell.

8. The instrument probe assembly of claim 6 wherein said tubular member also bears a temperature sensitive element in circuit with said sensing electrode.

9. The instrument probe assembly of claim 8 wherein said temperature sensitive element is a thermistor.

10. The instrument probe assembly of claim 1 secured to a tubular cap member to define therein a closed chamber.

11. The instrument probe assembly of claim 10 wherein said cap and housing are received in the central opening of an annular flotation collar.

* * * * *